Oct. 2, 1962 S. T. FAIR Plant Pat. 2,178
SUMMER APPLE
Filed Feb. 19, 1959
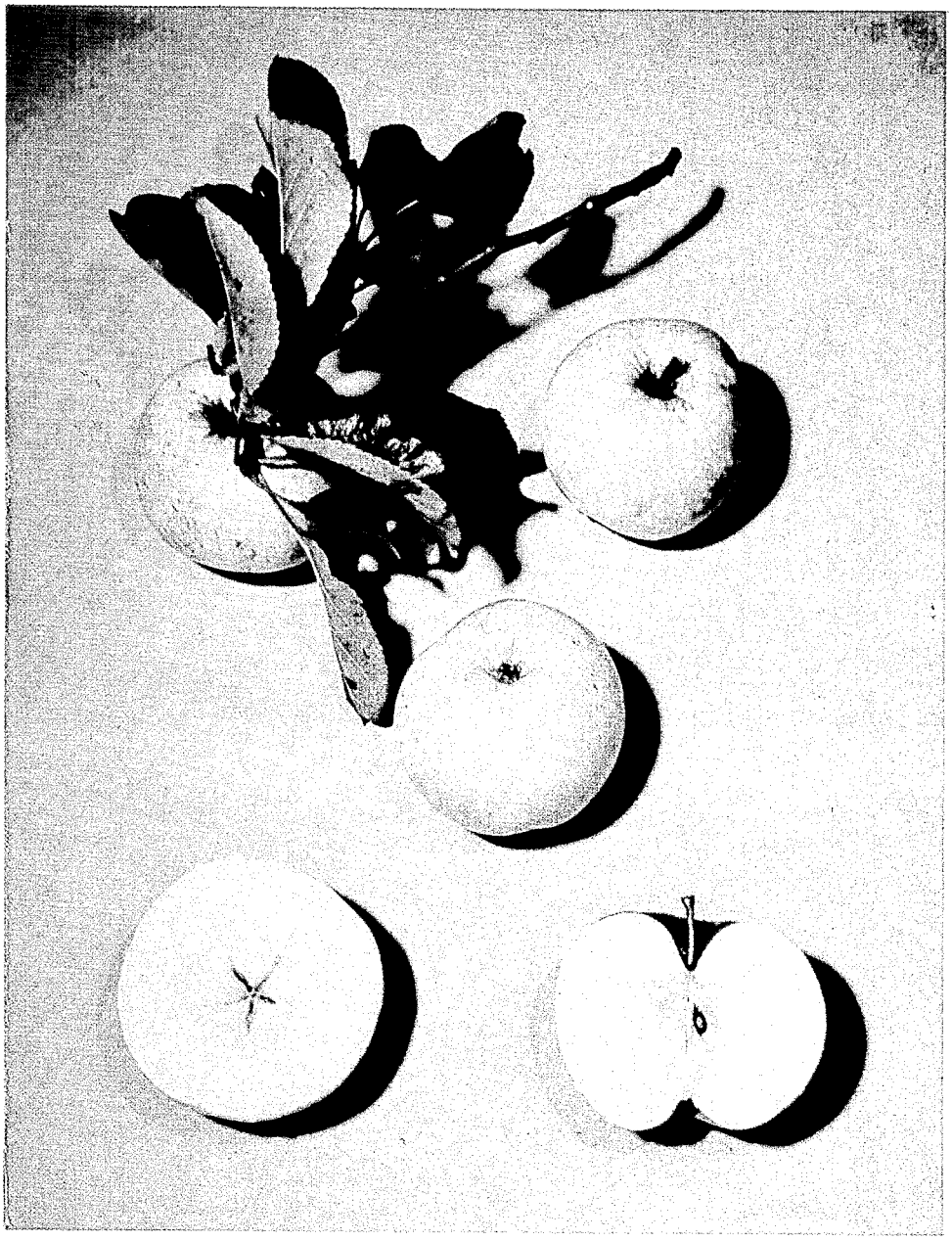
Inventor
Sara Iena Fair United States Patent Office Plant Pat. 2,178
Patented Oct. 2, 1962

2,178
SUMMER APPLE

Sara Tena Fair, Ingham County, Mich.
(Rte. 4, Mason, Mich.)

Filed Feb. 19, 1959, Ser. No. 794,484
1 Claim. (Cl. 47—62)

My invention introduces a new and promising variety of apple tree discovered by me.

The apple tree originated from seed saved from some apples which my father, John William Bennett, planted in the garden on his farm in section 7, Alaiedon Township, Ingham County, Michigan, approximately one mile south of Michigan State University lands, or eight and one half miles southeast of Lansing, Michigan, about the year 1921.

As some of the seedlings grew and produced apples, I discovered the merits of one tree with outstanding apples. In 1934 I asexually reproduced the tree by using a sprout from the roots of the original apple tree in the following manner: I mounded soil around this sprout to encourage development of roots and subsequently detached this rooted sprout and planted it at 2886 Phillips Road, Mason, Ingham County, Michigan, said location being approximately six miles north of the city of Mason, where the resultant tree is still standing. The tree and apples developed true to the original. Comparatively, my new variety is a hardy vigorous tree. Although the new invention has not been tested to determine its full value it is sufficiently promising to be worthy of note.

The new variety developed under Ingham County, Michigan, conditions is as accurately described as is reasonably possible on average characteristics which it exhibits. Color terminology is in accordance with the Dictionary of Color, Maerz and Paul, second edition, McGraw and Hill, except where general color terms are obvious:

Tree: Medium size; vigorous; hardy and healthy; erect; rounded head; somewhat spreading; bearing almost annually.

*Trunk.*—Moderately smooth; moderately thick.

*Branches.*—Moderately smooth; moderately thick.

*Twigs.*—Short to medium; many spurs; color—Brown Sugar, page 53, Plate 15, H–11. Lenticels—very slightly raised; medium number; small and quite inconspicuous.

*Buds.*—Obtuse, moderately free from branch; plump; slightly pubescent.

*Leaves.*—Medium to large size (width up to and including 3½ inches; length up to and including 5½ inches); medium thin; taper pointed with tendency to curl; roguse. Color—Art Green, page 67, Plate 22, L–7. Margin—crenate; moderately coarse serrate; on young trees occasionally double serrate. Petiole—average length 1¼ to 1½ inches; medium thickness.

Flowers: Medium early (first bloom about May 5–7; full bloom about May 10–12); large size; showy; 2½ to 2⅝ inches across; a perfect blossom in clusters of 6, 5 petals, 20 stamens, and 5 lobes on pistel stigma. Color—white with Rhododendron tinge, page 131, Plate 54, J–6.

Fruit: When immature, Lettuce Green, page 63, Plate 10, L–5, with Rhododendron blush, page 131, Plate 54, J–6. Summer apple maturity season—August and September, often keeping over in October. Usually fruit hangs pretty well to the tree. Apples are more apt to be borne singly, a few in clusters. Tree bears moderate to sometimes heavy crops of fruit.

*Size.*—Axil diameter approximately 2⅝ inches, and transverse diameter approximately 3⅛ inches for average fruit.

*Shape.*—Uniformly globose.

*Stem.*—Moderately thick; about one inch long; sometimes slightly clubbed.

*Stem cavity.*—Apex is obtuse; russeted; depth about ⅜ inch; breadth about ⅕ inch.

*Stem basin.*—Radiating delicately russeted flaring base; somewhat wavy; depth about ½ inch; breadth about 1¼ inches.

*Calyx.*—Closed to partially open and sometimes reflexes; tapered downward; depth about ⅜ inch; moderately pubescent.

*Calyx eye.*—Open; depth about ⅜ inch; breadth 1⅛ inch; basin sometimes slightly wavy.

*Skin.*—Moderately thin; glossy; waxen, quite evenly spaced dots of Reed Yellow, page 43, Plate 10, I–1; slightly submerged. Sometimes there are also a few russet dots. Ground color—Chalcedony Yellow, page 59, Plate 18, J–1. Color markings—blush on most of the apples usually nearer the stem end; color—Rhododendron, page 131, Plate 54, J–6. Bloom—overspread with a delicate bloom. Prevailing effect—attractive yellow with bright blush.

*Calyx tube.*—Moderate size; somewhat urn-shaped.

*Core.*—Median; distinct in cross section; somewhat heart-shaped. Bundle area—medium size; symmetrical; acute at the eye. Halves of core—equal; color—Marguerite Yellow, page 43, Plate 10, C–1. Core line clasping; in some seasons there is a tendency to firm transparent spots in some of the fruits. Carpels—5; axile; usually closed, sometimes open; lining of seed cavity tough; about ½ inch long and ¼ inch in breadth; color—Sulphur Yellow, page 43, Plate 10, J–1. Longitudinal section—oval; acute at apex.

Seeds: Length about 5/16 inch; width about ¼ inch; sometimes numerous; other times the seeds do not all develop. Form—orbicular at one end, acuminate at the other. Color—Weathered Oak, page. 39, Plate 8, L–11.

Flesh: Not juicy; color—Oyster White, page 43, Plate 10, B–1, astringent until ripe. When fully ripe the texture is mellow; flavor zesty; aroma charming; general rating, good to best.

Use: For all culinary purposes; especially good for apple pies; admirably adapted for canning and apple sauce. When fully ripe, pleasing eaten raw.

Keeping quality: Good to best for a summer apple variety.

I claim:

A new and distinct variety of apple tree, substantially as herein shown and described, characterized particularly as to novelty by its Rhododendron tinge on the blossoms following through to maturity on the blush of the apples.

References Cited in the file of this patent

UNITED STATES PATENTS

P.P. 1,805 Frazier ---------- Feb. 3, 1959